United States Patent [19]
Ehrhardt et al.

[11] Patent Number: 6,063,752
[45] Date of Patent: May 16, 2000

[54] ACYLATED CARBOXYL ALKYL SACCHARIDES, METHOD FOR MANUFACTURE AND USE THEREOF IN DETERGENTS

[75] Inventors: Sonja Ehrhardt, Gross-Gerau; Alireza Haji Begli, Ramsen; Markwart Kunz, Worms, all of Germany

[73] Assignee: Sudzucker Aktiengesellschaft Mannheim/Ochsenfurt, Gross-Gerau, Germany

[21] Appl. No.: 08/878,384

[22] Filed: Jun. 18, 1997

[30] Foreign Application Priority Data

Jun. 19, 1996 [DE] Germany .......................... 196 24 345

[51] Int. Cl.$^7$ .............................. C07H 15/04; C11D 1/66; C11D 1/04
[52] U.S. Cl. ........................ 510/470; 536/1.11; 536/18.5; 536/18.6; 536/66; 536/68; 536/72; 536/108; 536/116; 536/123.1; 536/123.13; 536/124; 510/471; 510/376; 510/531; 510/533; 510/312; 510/361; 8/137; 8/107; 8/111; 252/186.38; 252/186.4
[58] Field of Search ................... 536/1.11, 18.3, 536/18.5, 18.6, 66, 68, 69, 72, 108, 116, 123.1, 123.13, 124; 510/470, 471, 376, 531, 533, 312, 361; 8/137, 107, 111; 252/186.38, 186.4

[56] References Cited

U.S. PATENT DOCUMENTS

| | | | |
|---|---|---|---|
| 4,520,182 | 5/1985 | Namikoshi | 536/66 |
| 4,873,322 | 10/1989 | Fechtig et al. | 536/4.1 |
| 5,686,426 | 11/1997 | Martel et al. | 514/25 |

FOREIGN PATENT DOCUMENTS 4402051  7/1995  Germany .

WO 97/34623  9/1997  WIPO .

OTHER PUBLICATIONS

Hackh's Chemical Dictionary, fourth edition, p. 132, McGraw–Hill, Inc. (month unknown), 1969.
Bateman et al., Electrophoresis, 17(12) pp. 1818–1828, Dec. 1996.
Binder et al, Monatshefte fur Chemie, 126, 923–931 (month unknown), 1995.
Dean et al, Carbohydrate Research, v. 245, pp. 175–192 (month unknown), 1993.

*Primary Examiner*—Alan Diamond
*Attorney, Agent, or Firm*—Darby & Darby

[57] ABSTRACT

Acylated carbohydrates with at least one carboxyalkyl group etherified with the carbohydrate of the following general formula

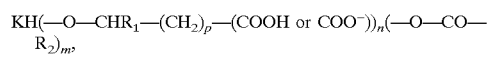

wherein KH (carbohydrate) is a monosaccharide, disaccharide, trisaccharide or polysaccharide, and wherein if KH is a monosaccharide, then n=1 to 4 and m=1 to 4 with n+m=2 to 5;

if KH is a disaccharide, then n=1 to 7 and m=1 to 7 with n+m=2 to 8;

if KH is a trisaccharide, then n=1 to 10 and m=1 to 10 with n+m=2 to 11; and if KH is a polysaccharide, then n=0.2 to 2.8 and m=0.2 to 2.8 with n+m=0.4 to 3 (with polysaccharide referred to the monosaccharide unit of the KH), and wherein R1 is=H or a moiety with 1–9 carbon atoms, in particular an alkyl or acyl moiety, and R2 is a moiety with 1–9 carbon atoms, in particular an alkyl or acyl moiety, and wherein p=0 to 9.

10 Claims, No Drawings

ACYLATED CARBOXYL ALKYL SACCHARIDES, METHOD FOR MANUFACTURE AND USE THEREOF IN DETERGENTS

BACKGROUND OF THE INVENTION

The present invention relates to acylated carboxyalkyl-saccharides, a method for manufacturing the compound as well as the use thereof in detergents as a complexing agent and bleaching agent activator.

Detergents generally contain tensides, bleaching agents, so-called builders as well as optical brighteners and accessory agents. The bleaching agents are provided for bleaching the materials to be washed, whereby the undesirable staining attendend materials are destroyed by oxidizing or reducing chemicals. Sodium perborate is frequently used as a bleaching agent which above 60° C. increasingly separates perhydroxyl anions in form of active oxygen, thereby being able to remove a variety of stains. At lower temperatures, however, the bleaching action is insufficient, so that so-called bleaching agent activators, such as tetraacetylethylendiamine are used. The activators are perhydrolized by the bleaching agents, setting free active bleaching species, such as per-acids.

The builders serve as complexing agents and predominantly eliminate calcium and magnesium ions.

Presently, the selection of ingredients in detergents useful as bleaching agent activators and builders, is mainly determined by issues relating to environmental protection and energy savings. For this reason, for example, activators based on renewable resources, such as carbohydrates, are employed which are more effective and biologically more compatible. There are also known from DE 2 149 737 and the U.S. Pat. No. 3,634,392 carboxymethylated oligosaccharides which are used in detergents as builders.

Because of their structural properties, the compounds derived from carbohydrates, however, are employed in detergents either only as complexing agents and builders, respectively, or only as bleaching agent activators. Consequently, the detergents require a separate substance for each of the two required functions.

SUMMARY OF THE INVENTION

It is among the objects of the present invention to provide compounds which simultaneously act as (co-)builders and bleaching agent activators, while being, at the same time, environmentally compatible and highly efficient.

According to one solution there are provided acylated carbohydrates with at least one carboxyalkyl group etherified with the carbohydrate of the following general formula

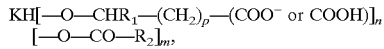

$$KH[-O-CHR_1-(CH_2)_p-(COO^- \text{ or } COOH)]_n$$
$$[-O-CO-R_2]_m,$$

wherein KH (carbohydrate) is a monosaccharide, disaccharide, trisaccharide, polysaccharide, such as polyglucane, in particular cellulose, starch or maltodextrin or polyfructane, in particular inulin, and wherein if KH is a monosaccharide, then n=1 to 4 and m=1 to 4 with n+m≦5;

if KH is a disaccharide, then n=1 to 7 and m=1 to 7 with n+m≦8;

if KH is a trisaccharide, then n=1 to 10 and m=1 to 10 with n+m≦11;

if KH is a polysaccharide, such as polyfructane or polyglucane, then n=0.2 to 2.8 and m=0.2 to 2.8 (referred to a monosaccharide unit) with n+m≦3, wherein $R_1$=H or a moiety with 1–9 carbon atoms, in particular an alkyl or acyl moiety, and $R_2$ a moiety with 1–9 carbon atoms, in particular an alkyl or acyl moiety, and wherein p=0–9.

The compounds of the present invention represent acylated carbohydrates with at least one carboxyalkyl group wherein through the combination of a carboxyalkyl group and an acyl group compounds are obtained which simultaneously have a high effectiveness as an activator and as a (co-)builder, a superior water solubility and excellent environmental compatibility. The at least one carboxyalkyl group $[-O-CHR_1-(CH_2)_p-(COO^- \text{ or } COOH)]$ is present in form of an acid (COOH) or a salt (COO$^-$) and is etherified with the carbohydrate via an oxygen atom. The at least one carboxyl group $[-O-CO-R_2]$ is esterified with the carbohydrate.

The invention also relates to acylated carbohydrates with at least one carboxyalkyl group wherein the carbohydrates are selected from the group of the monosaccharides, disaccharides, trisaccharides or polysaccharides, such as polyfructane, for example inulin, or polyglucane, for example cellulose, starch or maltodextrin, or polyfructane, as well as to their use in detergents as (co-)builders capable of simultaneously activating bleaching agents.

In a particularly preferred embodiment, as carbohydrates there are employed glucose, fructose, saccharose, palatinose, maltose, lactose, raffinose, trehalulose, polyfructane, inulin, polyglucane, cellulose, starch, maltodextrine or a mixture thereof.

In the context of the present invention, polysaccharides are understood to include, in particular, polyfructanes, such as inulin or polyglucanes, such as cellulose or starch, also broken down polysaccharides, meaning broken down polyfructanes or broken down polyglucanes. Broken down polyfructanes or broken down polyglucanes are generated by the dissociation of the polyglucanes or polyfructanes by enzymes or through acid catalysis, and are characterized by, for example, a lower viscosity and reduced chain lengths. The polyglucanes or polyfructanes can be dissociated until they reach a viscosity and/or chain length of the raw material as is desired for the derivate to be synthesized. According to the invention, the broken down polyfructanes or broken down polyglucanes are preferred raw material for the derivatization in accordance with the invention.

The number of carboxyalkyl groups per carbohydrate, meaning the degree of etherization DS, is 1 to 4 for monosaccharides, 1 to 7 for disaccharides, and 1 to 10 for trisaccharides. The degree of etherization DS is 0.2 to 2.8 for polysaccharides, referred here to the monosaccharide unit. In a particularly preferred way, degrees of etherization are 1 to 3 for di- and trisaccharides, from 0.2 to 2.8 for polysaccharides and 1 for monosaccharides. The carboxyalkyl group preferably comprises 1 to 11 carbon atoms and preferably is a carboxymethyl group or a carboxyethyl group.

The number of acyl groups per carbohydrate, meaning the degree of acylation, is 1 to 4 for monosaccharides, 1 to 7 for disaccharides, and 1 to 10 for trisaccharides. The degree of acylation is 0.2 to 2.8 for polysaccharides, referred here to the monosaccharide unit. In a particularly preferred mode, the carbohydrates comprising at least one carboxyalkyl group are completely acylated, meaning that all non-etherified hydroxy groups of the carbohydrate are acylated. The carboxyalkyl group are here unexpectedly and advantageously not altered. In a preferred embodiment, the acyl groups comprise 2 to 10 carbon atoms, in a particularly preferred embodiment 2 to 6 carbon atoms. The invention especially provides for the acetylation of the carboxyalkylated carbohydrates.

For preparing the compounds of the invention, carboxyalkylated carbohydrates can be prepared by etherifying α-halogen carbonic acids with carbohydrates (U.S. Pat. No. 3,634,392; DE 2 149 737, van Bekkum et al., Carbohydr. Res. 271 (1995), 101). The carboxyalkylated carbohydrates can also be prepared through a Michaelis-analog addition of carbohydrates to, for example, acrylnitril, followed by saparofication of the nitril group to the carboxyl group (U.S. Pat. Nos. 3,068,220; 3,161,359; AT 369 383). The preparation of CMC (carboxymethylcellulose) is described in C. V. Nikonovich et al., J. Polym. Sci. Symposium No. 42, 1625 (1973). The carboxyalkylated carbohydrates prepared in this manner can be acylated in several ways, especially completely acylated. Carbonic anhydrides or carbonic acid chlorides in the presence of various catalysts can be used as acylating agents. Surprisingly, the at least one carboxyalkyl group remains intact during acylation, so that the acylated, especially the completely acylated carbohydrates can be advantageously employed as bleaching agent activators and builders while retaining their water solubility provided by the acyl groups during the laundry process.

Among the α-halogen carbonic acids, the chloro and bromo-carbonic acids in particular play an important role for etherification. Carboxymethylization takes place in a strongly alkaline, aqueous solution at temperatures between 20° C. and 80° C., preferably between 20° C. and 50° C. The bases employed are inorganic bases, such as sodium hydroxide or potassium hydroxide. Carboxymethylization can be performed by adding carbohydrates to acrylnitril, followed by saporization of the nitril to acid. The addition reaction is carried out in a strongly alkaline solution at temperatures between 20° C. and 80° C., preferably between 30° C. and 50° C. The required alkalinity is attained by adding alkali hydroxides, such as sodium or potassium hydroxide. The hydrolysis of the nitril groups to the carboxyl group occurs preferably in two stages, wherein initially the amide is formed by hydrolysis with 30% hydrogen peroxide in a weak base solution at pH values between 8 and 9 and a reaction temperature of 50° C. and 60° C.; the reaction time ranges between 2 and 4 hours. The required alkalinity of the solution is attained by adding sodium hydroxide or potassium hydroxide. In a second stage, the amide is saporized at higher pH values between 12 and 14 to carbonic acid. The required alkalinity is here also attained by adding sodium hydroxide or potassium hydroxide. The reaction temperature is 20° C. to 50 ° C., preferably 20° C. to 30° C. The reaction time is at most 16 hours. With both methods, the degree of etherization DS is adjusted by the molar ratio carbohydrate (KH)—OH/ reagent and has to lie for trisaccharides between 1 and 10, for disaccharides between 1 and 7 and for monosaccharides between 1 and 4. If polysaccharides are employed as carbohydrates, then the degree of etherization DS is between 0.2 and 2.8, referred to a monosaccharide unit. The degree of etherization can be determined either by NMR spectroscopic methods or by titration.

The carboxyalkylated carbohydrates prepared in this manner, in particular the mono-, di- and trisaccharide derivates, are acylated with carbonic anhydrides from carbonic acids with 2 to 10, preferably 2 to 6, carbon atoms in the presence of organic bases, such as pyridin, 4-dimethylaminopyridin or inorganic bases, such as sodium acetate, or in the presence of Lewis acids, such as zinc chloride. Acylation of polysaccharides, such as—preferably broken down—cellulose or starch with the aforementioned carbonic anhydrides is preferably carried out in the presence of Brönstedt acids, such as sulfuric acid or acetic acid. Inulin derivates can be acylated with the help of Brönstedt acids or basic catalysts. The reaction temperature is set to a range between 0° C. and 70° C., with a reaction time of between 3 and 72 hours. Acylation can also be carried out with carbonic acid chlorides of carbonic acid with 2 to 10, preferably 2 to 6, carbon atoms in the presence of organic bases, such as pyridin or 4-dimethylaminopyridin at temperatures between 0° C. and 50° C., whereby temperatures of 0° C. to 20° C. are preferred. The degree of acylation is set by the ratio carboxyalkylated carbohydrate-OH/ reagent, wherein a partial or a complete acylation of the remaining OH groups can be carried out.

The compounds of the invention are identified by spectroscopic means: the characteristic frequencies of ester can be observed at about 1750, 1250 and 1080 cm$^{-1}$ and the frequencies of the carboxyalkyl group at about 1710 cm$^{-1}$ (IR spectroscopy). With proton NMR, the signals from the CH—CO—O group appear at about 2 ppm. With $^{13}$C NMR, the CO signals of both substituents appear in the region between 185 and 170 ppm.

The acylated carboxyalkylated carbohydrates of the present invention are particularly suited as activators for bleaching agents with builder properties for applications in formulations for laundry detergents.

The invention is explained in the following embodiments.

EXAMPLE 1

Complete acetylation of carboxymethyl-saccharose (DS 2) with zinc chloride as catalyst.

1.03 g dried zinc chloride is suspended in 24 ml acetanhydride; the mixture is cooled to 0° C. and mixed with 10 g carboxyethylated saccharose (DS 2). The reagent mixture is slowly heated to room temperature and hydrolized after 60 hours by adding 30 ml ice water. After extraction with dichloromethane and drying of the organic phase, completely acetylated carboxyethylated saccharose (DS 2) can be isolated, yielding 12.6 g (80% yield).

EXAMPLE 2

Complete acetylation of carboxyethylated saccharose (DS 2) in the presence of zinc chloride.

1.03 g dried zinc chloride is suspended in 24 ml acetanhydride; the mixture is mixed with 10 g carboxyethylated saccharose (DS 2) at a temperature of 0° C., then slowly heated to room temperature and is hydrolized after 60 hours by adding 30 ml ice water. After extraction with dichloromethane and drying of the organic phase, completely acetylated carboxyethylated saccharose (DS 2) can be isolated in form of a colorless solid with a yield of 84% (12.7 g).

EXAMPLE 3

Complete acetylation of carboxymethyl-glucose (DS 1) in the presence of sodium acetate.

The reagent mixture of 0.2 g sodium acetate, 24 ml acetanhydride and 2.5 g carboxymethyl-glucose is heated for 36 hours at 60° C. After the reagent solution has cooled down and the solvent is removed under vacuum, the raw product is dispersed in dichloromethane, the organic phase is purified with activated charcoal (Norit SK) and concentrated. Completely acetylated carboxymethyl-glucose (DS 1) is obtained with a yield of 75% (3.2 g).

EXAMPLE 4

Complete acetylation of carboxyethyl-glucose (DS 1) in the presence of sodium acetate.

The reagent mixture of 0.2 g sodium acetate, 24 ml acetanhydride and 2.5 g carboxyethyl-glucose (DS 1) is heated for 40 hours at 60° C. The reagent solution is left to cool down and the solvent is removed under vacuum. The residue is dispersed in dichloromethane, the organic phase is purified with activated charcoal (Norit SK) and the solvent is distilled off. The completely acetylated carboxyethyl-glucose (DS 1) is obtained with a yield of 75 % (3.1 g).

EXAMPLE 5

Partial acetylation of carboxymethyl-maltose (DS 2) with acetylchloride in pyridin.

7 ml acetylchloride are added dropwise to a solution of 5 g carboxymethyl-maltose in 30 ml pyridin at 0° C. After 2 hours at this temperature, the reagent mixture is poured into 40 ml ice water. The resulting solution is extracted several times with dichloromethane, the organic phase is purified with activated charcoal, dried and concentrated. Partially acetylated carboxymethyl-maltose (DS 2) (6.5 g) is isolated.

EXAMPLE 6

Partial acetylation of carboxyethyl-lactose (DS 2) with acetylchloride in pyridin.

7 ml acetylchloride are added dropwise to a solution of 5 g carboxyethyl-lactose in 30 ml pyridin at 0° C. After 2 hours at this temperature, the reagent mixture is poured into 40 ml ice water. The resulting solution is extracted several times with dichloromethane, the organic phase is purified with activated charcoal, dried and concentrated. Partially acetylated carboxymethyl-lactose (DS 2) (5.6 g) is obtained.

EXAMPLE 7

Complete acylation of carboxyethylated saccharose (DS 2) with caproic acid chloride in pyridin.

8.7 ml caproic acid chloride are added dropwise to a solution of 2 g carboxyethylated saccharose in 30 ml pyridin at 0° C. After 2 hours at this temperature, the reagent mixture is poured into 30 ml ice water. The resulting solution is extracted several times with dichloromethane, the organic phase is purified with activated charcoal (Norit SK) and concentrated. The completely acylated carboxyethylated saccharose (DS 2) is obtained with a yield of 70% (3 g).

EXAMPLE 8

Partial acetylation of carboxymethylinulin Na salt (CMI, DS 1) with acetanhydride/acetic acid.

To a suspension of 10 g (0.041 mole) CMI in 50 ml acetic acid, mixed with 0.3 ml concentrated sulfuric acid, a mixture of 10 ml acetic acid in 25 ml acetanhydride is added drop-wise with stirring at room temperature and then heated at 50° C. for 3 hours.

Through filtration, followed by neutral rinsing with acetone/water, the product is isolated in form of a white solid.

EXAMPLE 9

Partial acetylation of carboxymethylcellulose Na salt (CMC, DS 0, 65-0, 95) with acetanhydride/acetic acid.

To a suspension of 10 g CMC (Walocel CRT 30 GA, Wolff Walsrode) in 50 ml acetic acid, mixed with 0.3 ml concentrated sulfuric acid, a mixture of 10 ml acetic acid in 25 ml acetanhydride is added drop-wise with stirring at room temperature and then heated at 50° C. for 3 hours.

Through filtration, followed by neutral rinsing with acetone/water, the product is isolated in form of a white solid.

EXAMPLE 10

Partial acetylation of carboxymethyl-starch Na salt (CMSt, DS 1) with acetanhydride/acetic acid.

To a suspension of 10 g CMSt in 50 ml acetic acid, mixed with 0.3 ml concentrated sulfuric acid, a mixture of 10 ml acetic acid in 25 ml acetanhydride is added drop-wise with stirring at room temperature and then heated at 50° C. for 3 hours.

Through filtration, followed by neutral rinsing with acetone/water, the product is isolated in form of a white solid.

EXAMPLE 11

Activator test 0.026 g ethylenediamine-tetraacetic acid and the activator (0.08 M) are added to 1.15 g sodium perborate in 30 ml 0.1 N soda lye. After 30 minutes at 30° C., a 7.5 ml sample at 0° C. is rapidly added drop-wise to 8.75 ml 5% sulfuric acid. The mixture is titrated with 0.1 N cerium-(IV)-ammonium sulfate solution against ferroin (determination of the hydrogen peroxide concentration). Thereafter, the solution is mixed with 10 ml 10% potassium iodide solution and iodometrically titrated with 0.1 N sodium thiosulfate solution (determination of the per-acid concentration).

The results are represented in Table I.

Formation of peracetate (in mole %) in the presence of Na-Perborate in 0.1 N NaOH at 30° C. after 30 minutes Substance Mole % Substance Mole %

TABLE I

| Substance | Mole % |
|---|---|
| CMS (1)-acetate | 20 |
| CMS (2)-acetate | 18 |
| CES (1)-acetate | 20 |
| CES (2)-acetate | 19 |
| CML (2)-acetate | 20 |
| CMI (1)-acetate | 30 |
| CMC (0, 65–0, 95)-acetate | 26 |
| CEL (2)-acetate | 19 |
| CMM (2)-acetate | 18 |
| CEM (2)-acetate | 17 |
| CMG (1)-acetate | 21 |
| CEG (1)-acetate | 20 |
| CMSt (1)-acetate | 18 |

CMS (1)-acetate: completely acetylated carboxymethyl-saccharose with DS 1

CMS (2)-acetate: per-acetylated carboxymethyl-saccharose with DS 2

CES (1)-acetate: completely acetylated carboxyethyl-saccharose with DS 1

CES (2)-acetate: completely acetylated carboxyethyl-saccharose with DS 2

CML (2)-acetate: completely acetylated carboxymethyl-saccharose with DS 2

CEL (2)-acetate: completely acetylated carboxyethyl-lactose with DS 2

CMM (2)-acetate: completely acetylated carboxymethyl-maltose with DS 2

CEM (2)-acetate: completely acetylated carboxyethyl-maltose with DS 2

CMG (1)-acetate: completely acetylated carboxymethyl-glucose with DS 1

CEG (1)-acetate: completely acetylated carboxyethyl-glucose with DS 1

CMI (1)-acetate: Partially acetylated carboxymethyl-inulin with DS 1

CMC (0, 65-0, 95)-acetate: Partially acetylated carboxymethyl-cellulose with DS 0, 65-0, 95

CMSt (1)-acetate: Partially acetylated carboxymethyl-starch with DS 1

The mole % for the polysaccharides(CMI, CMSt, CMC) are referred to the monosaccharide unit.

The example demonstrates that at 30° C. the compounds of the invention produce active bleaching varieties, namely per-acids.

EXAMPLE 12

Complexing properties of the completely acylated carboxyalkylated compounds

The complexing ability of the compounds used according to the invention with respect to calcium ions was measured with Hampshire, a common test method for determining the complexing properties of components in laundry detergents with respect to calcium ions. The reagent solution of the activator test, 1.72 g completely acylated carboxymethylated saccharose (DS 1), 0.026 g ethylendiamin-tetraacetic acid and 1.15 g sodium perborate in 30 ml 0.1 N soda lye, is mixed after 30 minutes at 30° C. with 10 ml, 2 wt-% sodiumcarbonate solution, adjusted with 1N soda lye to pH 11 and filled up to 100 ml. This is followed by titration with 0.25 M calciumacetate solution until cloudy. The experimental results listed in Table II are based on an activator concentration of 0.08 molar solution.

TABLE II

| Substance | Quantity of Ca-carbonate (mg) |
|---|---|
| CMS (1)-acetate | 86 |
| CMS (2)-acetate | 98 |
| CES (1)-acetate | 82 |
| CMG (1)-acetate | 41 |
| CMI (1)-acetate | 96 |
| CMC (0, 65–0, 95)-acetate | 56 |

The example demonstrates that the compounds activating the bleaching agents can be at the same time advantageously employed as complexing agents.

The following examples 10 and 11 demonstrate that carbohydrates which have only one carboxyalkyl group or which are only acylated, can either only activate the bleaching agent or only perform complexing, whereas the compounds of the invention advantageously possess both those properties simultaneously.

EXAMPLE 13

Activator and Hampshire test with carboxyethylated saccharose 1.15 g sodium perborate in 30 ml 0.1 N soda lye are mixed first with 0.026 g ethylendiamin-tetraacetic acid and thereafter with 1.16 g carboxyethylated saccharose (DS 2). After 30 minutes at 30° C., the per-acid concentration is iodometrically measured from a 3 ml sample, as described above. The per-acid concentration is about 2 mole %.

From the same reagent solution and also after 30 minutes at 30° C., the calcium binding capacity is determined with Hampshire; the binding capacity is about 91 mg calciumcarbonate/1 g substance.

EXAMPLE 14

Activator and Hampshire test with saccharose-octaacetate 1.15 g sodium perborate in 30 ml 0.1 N soda lye are mixed first with 0.026 g ethylendiamin-tetraacetic acid and thereafter with 1.63 g saccharose-octaacetate. After 30 minutes at 30° C., the per-acid concentration is iodometrically measured from a 3 ml sample, as described above. The per-acid concentration is about 12 mole %.

From the same reagent solution and also after 30 minutes at 30° C., the calcium binding capacity is determined with Hampshire; the binding capacity is about 91 mg calcium carbonate/1 g substance.

What is claimed is:

1. Acylated carbohydrates with at least one carboxyalkyl group etherified with the carbohydrate of the following general formula

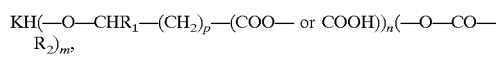

wherein KH is selected from the group consisting of monosaccharide, disaccharide, trisaccharide and polysaccharide, and wherein if KH is a monosaccharide, then n=1 to 4 and m=1 to 4 with n+m=2 to 5;

if KH is a disaccharide, then n=1 to 7 and m=1 to 7 with n+m=2 to 8;

if KH is a trisaccharide, then n=1 to 10 and m=1 to 10 with n+m=2 to 11;

if KH is a polysaccharide then KH is selected from the group consisting of a polyfructane, starch, and maltodextrins, and referenced to a monosaccharide unit n=0.2 to 2.8 and m=0.2 to 2.8, with n+m=0.4 to 3, and wherein $R_1$ is selected from the group consisting of H, a moiety with 1–9 carbon atoms, an alkyl, and acyl moiety, and $R_2$ is selected from the group consisting of a moiety with 1–9 carbon atoms, an alkyl and acyl moiety, and wherein p=0 to 9.

2. The carbohydrates according to claim 1, wherein the KH is selected from the group consisting of glucose, fructose, saccharose, maltose, palatinose, raffinose, lactose, and trehalulose.

3. The carbohydrates according to claim 1, wherein if KH is a monosaccharide, then n=1; if KH is a di- or trisaccharide, then n=1 to 3; and if KH is a polysaccharide, then referenced to a monosaccharide unit n=0.2 to 1.

4. The carbohydrates according to claim 1, wherein all non-etherified hydroxy groups of said general formula are at least one of completely acylated and completely acetylated.

5. The carbohydrates according to claim 1, wherein $R_1$ is equal to H with p being one of 0 and 1.

6. A method for preparing acylated carbohydrates with at least one carboxyalkyl group, wherein said carbohydrates are selected from the group consisting of glucose, fructose, saccharose, maltose, palatinose, raffinose, lactose, trehalulose, a polyfructane, starch, and maltodextrins, comprising the step of reacting carboxyalkylated carbohydrates with one of carbonic anhydrides and carbonic acid chlorides in the presence of a catalyst.

7. The method according to claim 6, wherein the carboxyalkyl group is selected from the group consisting of a carboxymethyl group and a carboxyethyl group, and wherein one of carbonic anhydrides and carbonic acid chlorides from $C_2$ to $C_{10}$ carbonic acids are used.

8. The method according to claim 6, wherein the catalyst is selected from the group consisting of pyridin, 4-dimethylaminopyridin, sodium acetate, zinc chloride and a Brönstedt acid.

9. The method according to claim 7, wherein one of carbonic anhydrides and carbonic acid chlorides from $C_2$ to $C_6$ carbonic acids are used.

10. A method for activating a bleaching agent in a laundry detergent composition which comprises contacting said detergent with an acylated carbohydrate containing at least one carboxyalkyl group, wherein said acylated carbohydrate containing at least one carboxyalkyl group functions as a complexing agent and simultaneously activates said bleaching agent.

* * * * *